(12) United States Patent
Shigetou et al.

(10) Patent No.: US 6,300,480 B1
(45) Date of Patent: *Oct. 9, 2001

(54) DYE-LABELED PROTEIN CONJUGATE AND METHOD FOR PREPARING THE SAME

(75) Inventors: Nobuyuki Shigetou, Hirakata; Jinsei Miyazaki, Higashiosaka; Hiroshi Nakayama, Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/310,851

(22) Filed: May 13, 1999

Related U.S. Application Data

(63) Continuation-in-part of application No. 08/831,204, filed on Apr. 2, 1997, now Pat. No. 5,922,618, and a continuation-in-part of application No. 08/745,337, filed on Nov. 8, 1996, now Pat. No. 5,965,713.

(30) Foreign Application Priority Data

May 14, 1998 (JP) .................................... 10-132418

(51) Int. Cl.⁷ .............................. C07K 17/02; C07K 1/13; G01N 33/533
(52) U.S. Cl. ................. 530/391.5; 436/800; 530/391.3; 530/402; 530/404; 530/405
(58) Field of Search .............. 530/391.3, 391.5, 530/402, 404, 405; 436/800

(56) References Cited

U.S. PATENT DOCUMENTS

| | | |
|---|---|---|
| 4,153,417 | 5/1979 | Hallgren et al. . |
| 5,650,334 | 7/1997 | Zuk et al. . |
| 5,714,386 | 2/1998 | Roederer . |
| 5,922,618 * | 7/1999 | Shigetou et al. ..................... 436/532 |
| 5,965,713 * | 7/1999 | Shigetou et al. ..................... 530/402 |

FOREIGN PATENT DOCUMENTS

| | | |
|---|---|---|
| 0800083 | 8/1997 | (EP) . |
| 08259826 A * | 10/1996 | (JP) . |
| 09132725 | 5/1997 | (JP) . |
| WO 9403631 | 2/1994 | (WO) . |
| WO 9506483 | 9/1995 | (WO) . |

OTHER PUBLICATIONS

Bajyanason et al, Derwent–Acc–No: 1990–224610, 1990.*
Spector, D.L.: "Fluorescent labeling of antibodies and DNA probes", 1998, Cold Spring Harbour Laboratory Press, vol. 2 of "Cells: a Laboratory Manual"; "Light Microscopy and Cell Structure", pp. 82.1–82.7; table 82.1.
Mujumdar R B, et al: "Cyanine Dye Labeling Reagents: Sulfoindocyanine Succinmidyl Esters" Bioconjugate Chemistry, US, American Chemical Society, Washington, vol. 4, No. 2, pp. 105–111.

* cited by examiner

Primary Examiner—Mary E. Ceperley
(74) Attorney, Agent, or Firm—McDermott, Will & Emery

(57) ABSTRACT

The present invention provides a dye-labeled protein conjugate in which a protein conjugate is labeled with a large number of dye molecules. In the dye-labeled protein conjugate, a protein conjugate that includes a protein and an antibody bound thereto via a disulfide bond is labeled with a cyanine dye represented by the formula (1) given below.

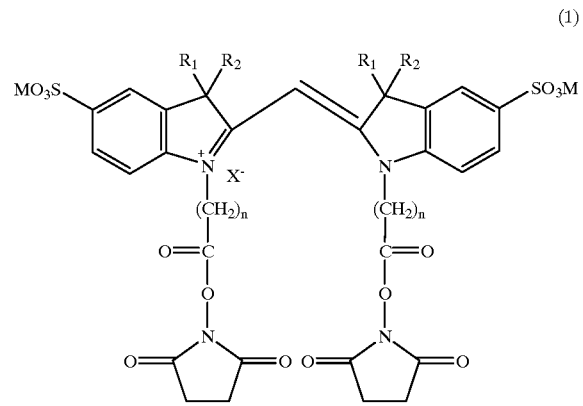

(1)

where $R_1$ and $R_2$ denote hydrogen or an alkyl group, X denotes a halogen, M denotes hydrogen or an alkali metal, and n represents an integer in a rage of 1 to 4.

3 Claims, No Drawings

DYE-LABELED PROTEIN CONJUGATE AND METHOD FOR PREPARING THE SAME

CROSS REFERENCES TO RELATED APPLICATIONS

This application is a continuation-in-part of application Ser. No. 08/831,204 filed Apr. 2, 1997, now U.S. Pat. No. 5,922,618 and a continuation-in-part of application Ser. No. 08/745,337 filed Nov. 8, 1996, now U.S. Pat. No. 5,965,713.

BACKGROUND OF THE INVENTION

The present invention relates to a dye-labeled protein conjugate prepared by binding an antibody to a protein to form a protein complex or conjugate and labelling the conjugate with a cyanine dye, and further to a method for preparing the same.

The dye-labeled antibody, which is obtained by labeling an antibody with a dye, specifically reacts with an antigen included in a sample solution and is readily recognizable with naked eyes. The dye-labeled antibodies are accordingly applied for immunosensors, each of which takes advantage of an immunological antigen-antibody reaction to detect a target substance included in a sample solution, and are used for diagnoses in a variety of medical institutions.

Cyanine dyes having the high molar absorption coefficient and the high reactivity are often used to label antibodies (Bioconjugate Chemistry Vol. 4, No. 2, pp105–111, 1993).

The functional group of the cyanine dye reacts with and is covalently bound to an amino group or a carboxyl group included in an antibody, and 20 to 50 molecules of the dye are attached to one molecule of the antibody.

The cyanine dye-labeled antibody thus prepared generally has high visual recognizability, and is effectively applied for, for example, immunochromatography to detect a small amount of a specific substance, such as human chorionic gonadotropin (HCG) that is present only in the urine of pregnant women.

The antibody generally includes several hundreds to several thousands of amino group or carboxyl group. The antibody has a three-dimensional steric configuration and thereby has only 50 groups that are related to the reaction. Namely only 50 molecules of the dye are bound to one molecule of the antibody.

When the dye-labeled antibody is applied for an immunosensor, it is accordingly difficult to detect a target substance having a low concentration.

BRIEF SUMMARY OF THE INVENTION

The object of the present invention is thus to provide a dye-labeled protein conjugate that is labeled with a large number of dye molecules.

Another object of the present invention is to provide a method for preparing the dye-labeled protein conjugate.

The present invention provides a dye-labeled protein conjugate comprising a protein, an antibody bound to the protein via a disulfide bond to form a protein conjugate, and a cyanine dye represented by the formula (1) given below, the protein conjugate being labeled with the cyanine dye.

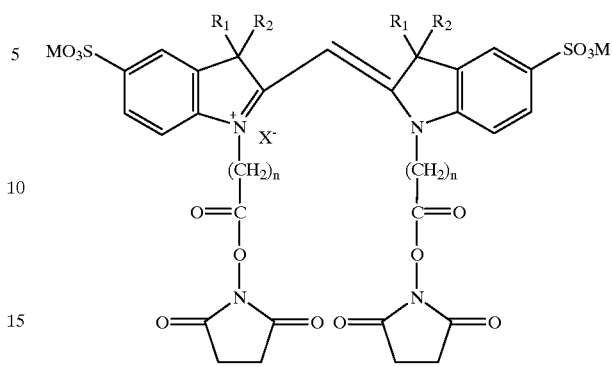

(1)

where $R_1$ and $R_2$ denote hydrogen or an alkyl group, X denotes a halogen, M denotes hydrogen or an alkali metal, and n represents an integer of 1 to 4.

Binding a protein to the antibody extends the area of the antibody that can be linked with the cyanine dye, and thereby increases the number of cyanine dye molecules bound to the protein conjugate, compared with a single body of the antibody. The number of dye molecules bound to one molecule of the antibody in the protein conjugate is, for example, about 10 times that of the antibody in the single body. The dye-labeled protein conjugate accordingly has high visual recognizability.

When the dye-labeled protein conjugate of the present invention is applied for, for example, immunochromatography, the immunochromatography can detect a target substance (sample) with high sensitivity even when the sample has a low concentration. Because of the high sensitivity, the dye-labeled protein conjugate of the present invention is applicable for biosensors.

In accordance with one preferable application of the dye-labeled protein conjugate of the present invention, a skeleton of the cyanine dye is bound to the protein conjugate via a covalent bond of an acyl carbon originated from a succinimidyl group in the cyanine dye with a nitrogen originated from an amino group in the protein conjugate.

The present invention is also directed to a method for preparing a dye-labeled protein conjugate. The method comprises the steps of: reducing a protein in a neutral or weak alkaline phosphate buffer solution; adding an antibody to the buffer solution to prepare a protein conjugate; and adding a cyanine dye represented by the formula (1) given above to the buffer solution to label the protein conjugate with the cyanine dye.

The present invention is further directed to another method for preparing a dye-labeled protein conjugate. The method comprises the steps of: reducing a protein in a neutral or weak alkaline phosphate buffer solution; adding a cyanine dye represented by the formula (1) given above to the buffer solution to label the reduced protein with the cyanine dye; and adding an antibody to the buffer solution to make the antibody bound to the reduced protein.

In accordance with one preferable application, the method includes the step of labeling the antibody with succinimidyl pyridyl dithiopropionate represented by the formula (2) given below in a neutral or weak alkaline phosphate buffer solution, prior to the step of making the antibody bound to the reduced protein.

In any of the above methods, it is preferable that the phosphate buffer solution has a pH value in a range of 7.0 to 8.0.

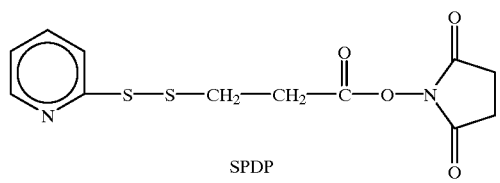

SPDP (2)

The antibody used to prepare the dye-labeled protein conjugate of the present invention is not specifically restricted, but may have a variety of origins and sub-classes. Available examples of the antibody include immunoglobulins (Ig), such as mouse IgG, mouse IgM, mouse IgA, mouse IgE, rat IgG, rat IgM, rat IgA, rat IgE, rabbit IgG, rabbit IgM, rabbit IgA, rabbit IgE, goat IgG, goat IgM, goat IgE, goat IgA, sheep IgG, sheep IgM, sheep IgA, and sheep IgE. These antibodies may be of commercial origin or directly collected from the corresponding animals.

The protein bound to the antibody may be any protein that does not exert the function as the antibody. The protein having high solubility in water is especially preferable. For example, serum-originated albumin that does not inhibit the reaction of the antibody and has high water solubility is preferably used.

The cyanine dye represented by the formula (1) is a red dye readily recognizable with naked eyes. The cyanine dye has a less number of conjugated carbons and thereby has the highest solubility in water among a variety of cyanine dyes.

The halogen represented by X in the formula (1) may be fluorine, chlorine, bromine, or iodine. The metal represented by M may be lithium, sodium, or potassium.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

The following describes the mechanism of binding the cyanine dye to the antibody.

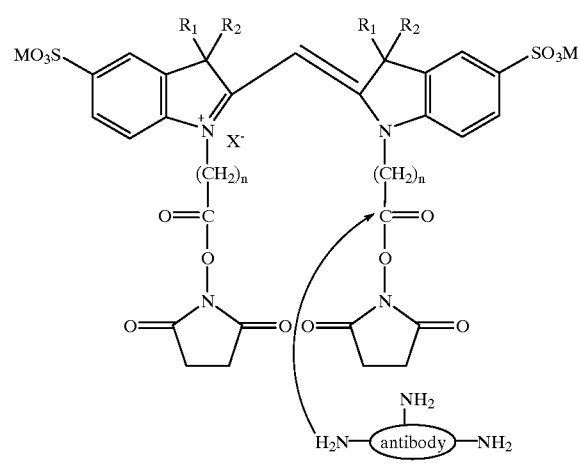

(3)

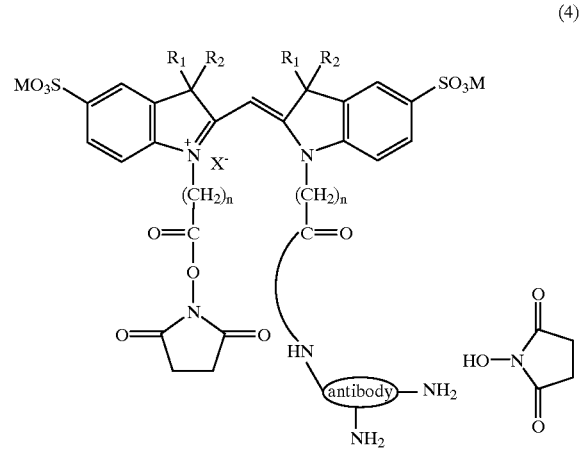

(4)

When the antibody is mixed with the cyanine dye having a succinimidyl group, an amino group in the antibody approaches an ester bond of the succinimidyl group in the dye as shown by the formula (3).

The amino group reacts with the ester bond as shown by the formula (4), so that one hydrogen atom is released from the amino group. The hydrogen atom released from the amino group is attached to succinimide in the succinimidyl group. Succinimide is then changed to hydroxysuccinimide, which is released from the succinimidyl group. At the same time, the residue of the succinimidyl group and the hydrogen atom-released amino group combine to form an amide bond, through which the dye is linked with the antibody.

The following describes one exemplified process of synthesizing the cyanine dye represented by the formula (1) given above.

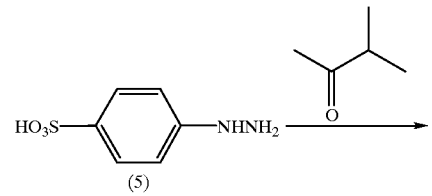

(5)

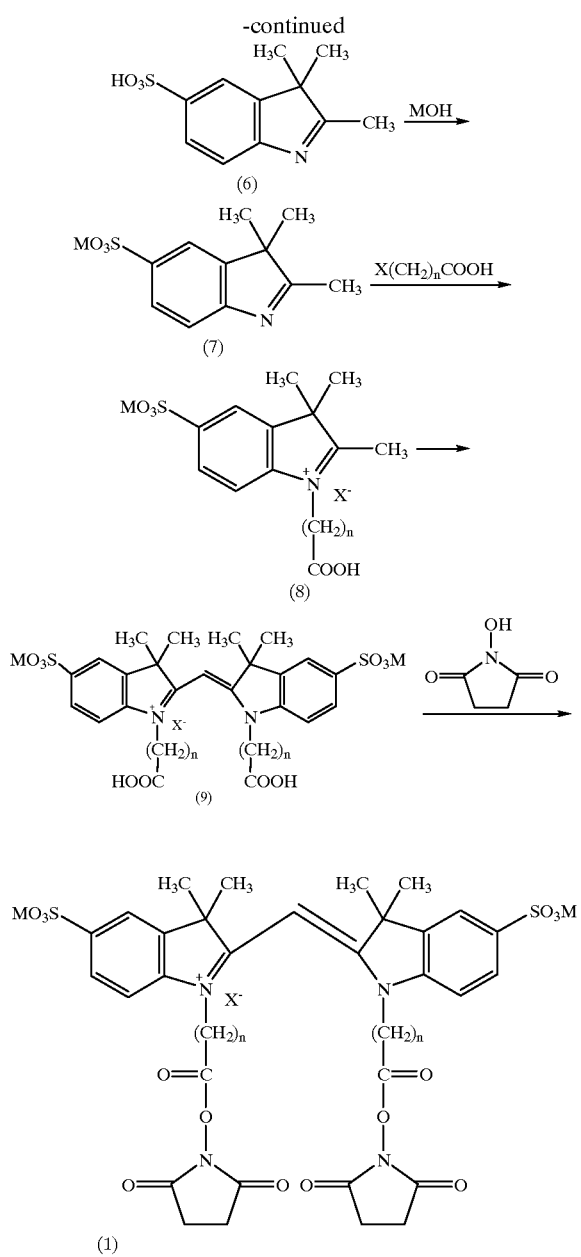

The process first dissolves hydrazinobenzenesulfonic acid (5) and isopropyl methyl ketone in an acidic solvent and heats the mixture to obtain indoleniumsulfonate (6). The process then adds a metal hydroxide-saturated alcohol solution into an alcohol solution of indoleniumsulfonate (6), so as to yield a metal salt of indoleniumsulfonate (7).

The process subsequently adds a halogenized fatty acid to an organic solvent solution of the metal salt (7) and heats the mixture to obtain a metal salt of carboxyalkylindoleniumsulfonate (8). By taking into account the solubility in water, it is preferable that the halogenized fatty acid has one to four carbon atoms.

The process then dissolves the metal salt (8) and N-carboxyethyl-3, 3-dimethylindolenine into a basic organic solvent and heats the mixture to prepare a carboxylic acid derivative (9). The process subsequently adds hydroxysuccinimide and dicyclohexylcarbodiimide as a condensing agent to the organic solvent solution of the carboxylic acid derivative (9) and well stirs the mixture to yield the cyanine dye represented by the formula (1).

The halogen included in the respective compounds represented by the formula (1), the formula. (8), and the formula (9) may be fluorine, chlorine, bromine, or iodine. The metal included in the respective compounds represented by the formula (1) and the formulae (7) through (9) may be lithium, sodium, or potassium.

The present invention is described more in detail with concrete examples.

EXAMPLE 1

(1) Labeling Mouse IgG with Succinimidyl Pyridyl Dithiopropionate

The process first dissolved 5 mg ($3.3 \times 105$ mmol) of mouse IgG (hereinafter simply referred to as IgG) into 2 ml of a phosphate buffer solution(hereinafter referred to as PBS). The process then added dropwise 0.1 ml of an ethanol solution containing succinimidyl pyridyl dithiopropionate (hereinafter referred to as SPDP) with stirring at room temperature. The ethanol solution of SPDP added dropwise contained 0.52 mg ($1.67 \times 10^{-3}$ mmol) of SPDP.

After stirring the mixed solution at room temperature for 30 minutes, the process filtered the mixed solution through a Sepharose gel (manufactured by Pharmacia Fine Chemical Inc., Sephadex G25M column). This gave approximately 6 ml of the PBS solution containing SPDP-labeled IgG (hereinafter referred to as IgG-SPDP). The concentration of the PBS solution thus obtained and the number of SPDP molecules bound to the antibody were determined by the process discussed below.

The procedure collected 0.5 ml of the PBS solution and measured the absorbance at 280 nm. The observed absorbance was 1.25.

The procedure then added 0.025 ml of an aqueous solution containing 100 mM dithiothreitol (hereinafter referred to as DTT) to the PBS solution. After the mixed solution was stood still for one minute, the absorbance was measured at 343 nm. The observed absorbance was 0.39.

Since IgG does not have absorption at 343 nm, the observed absorbance at 343 nm is attributed to thiopyridone released by reduction with DTT. The released thiopyridone is obtained by reducing a pyridyldithio group in the SPDP. The concentration of the released thiopyridone is identical with the concentration of the SPDP bound to the antibody. The concentration [SPDP] of the SPDP is thus determined by the following equation. Here the molar absorption coefficient of thiopyridone at 343 nm is set equal to $8.08 \times 10^3$.

$$[SPDP]=0.39/(8.08\times10^3)=4.83\times10^{-5}(M)$$

The observed absorbance at 280 nm is originated from IgG. The bound SPDP, however, also has absorption at 280 nm. The concentration [IgG] of IgG is accordingly determined by subtracting the effect of this absorption. Here $Ab_{280,IgG}$ represents the absorbance attributed to IgG at 280 nm, the molar absorption coefficient of SPDP at 280 nm is set equal to $5.1 \times 10^3$, and the molar absorption coefficient of IgG at 280 nm is $2.10 \times 10^5$.

$$Ab_{280,IgG}=1.25-(4.83\times10^5\times5.1\times10^3)=1.00$$

$$[IgG]=1.00/(2.10\times10^5)=4.78\times10^{-6}\ (M)$$

The number of SPDP molecules bound to one IgG molecule is accordingly given by:

$$[SPDP]/[IgG]=4.83\times10^{-5}/4.78\times10^{-6}=10.1$$

(2) Reducing Bovine Serum Albumin with Dithiothreitol

The process dissolved 110 mg of bovine serum albumin (hereinafter referred to as BSA) in 10 ml of PBS, added 77 mg of DTT dissolved in 1 ml of PBS to the serum albumin-PBS solution, and stirred the mixed solution at room temperature for 15 minutes. The process quickly filtered the mixed solution through a gel, Sephadex G25M column. This gave approximately 24 ml of the PBS solution containing BSA (SH-free).

(3) Preparing Protein Conjugate (IgG-SPDP-BSA)

The (SH-free) BSA solution was quickly mixed with the PBS solution (6 ml) containing IgG-SPDP. After the mixed solution was stood still at 4° C. for 20 hours, the process dialyzed the mixed solution against 20 liters (5 liters×4) of a PBS solution containing sodium azide as an antiseptics (hereinafter referred to as PBS.Az), in order to remove unreacted BSA. This gave approximately 25 ml of the PBS solution containing IgG-SPDP-BSA.

(4) Labeling Protein Conjugate (IgG-SPDP-BSA) with Dye

The process dissolved 122.7 mg of the cyanine dye represented by the formula (1) into 1 ml of PBS (400 equivalents of the total protein quantity) to obtain a dye solution (hereinafter referred to as SLIC1). The cyanine dye included iodine as X, potassium as M, and 2 carbon atoms as n in the formula (1).

The process slowly added the SLIC1 dropwise to the IgG-SPDP-BSA solution (total protein quantity: $3.18\times10^{-4}$ mmol) obtained in the process (3). After the mixed solution was stood still at 4° C. for 20 hours, the process dialyzed the mixed solution against 20 liters of the PBS.Az, in order to remove unreacted dye molecules. This gave approximately 26 ml of the PBS solution containing the SLIC1-labeled protein conjugate. The number of SLIC1 molecules bound to one molecule of the protein conjugate in the SLIC1-labeled protein conjugate was determined according to the following procedure.

The observed absorbance of the resultant solution was 80 at 430 nm. The IgG-SPDP-BSA does not have absorption at 430 nm, so that the observed absorbance at 430 nm is attributed to the SLIC1 bound to the protein conjugate. The concentration[SLIC1] of the SLIC1 is thus determined by the following equation. Here the molar absorption coefficient of SLIC1 at 430 nm is set equal to $1\times10^5$.

$$[SLIC1]=80/1\times10^5=8.0\times10^{-4}\ (M)$$

The number of SLIC1 molecules bound to one molecule of the protein conjugate is calculated by the following equation:

$$[SLIC1]/[IgG]=8.0\times10^{-4}/1.06\times10^{-6}=755$$

where the concentration [IgG] of IgG in the PBS solution containing the SLIC1-labeled protein conjugate is set equal to $1.06\times10^{-6}$ M (on the assumption that there is no loss of IgG in each step after the SPDP labeling).

EXAMPLE 2

(1) Labeling IgG with SPDP

IgG was labeled with SPDP according to the method discussed in Example 1. The total volume was 6 ml, the concentration of IgG was $4.10\times10^{-6}$ M, and the number of SPDP molecules per one IgG molecule was 11.5.

(2) Preparing BSA-SLIC1

The process dissolved 110 mg ($1.62\times10^{-3}$ mmol) of BSA into 10 ml of PBS, and slowly added 1 ml of the SLIC1 dropwise to the PBS solution with stirring at room temperature. The SLIC1 added dropwise contained 162.7 mg (0.162 mmol, 100 equivalents) of the dye identical with that of Example 1.

After being stirred overnight at 4° C., the mixed solution was dialyzed against 20 liters (5 liters×4) of the PBS.Az. This gave 6 ml of the PBS solution containing the SLIC1-labeled BSA. The concentration of the resultant solution and the number of SLIC1 molecules bound to one BSA molecule were determined according to the following procedure.

The observed absorbance of the resultant solution was 9.6 at 280 nm and 59.0 at 430 nm. The BSA does not have absorption at 430 nm, so that the observed absorbance at 430 nm is attributed to the SLIC1 bound to the BSA. The concentration [SLIC1] of the SLIC1 is thus determined by the following equation. Here the molar absorption coefficient of SLIC1 at 430 nm is set equal to $1\times10^5$.

$$[SLIC1]=59.0/1\times10^5=5.9\times10^{-4}\ (M)$$

The observed absorbance at 280 nm is originated from the BSA. The bound SLIC1, however, also has absorption at 280 nm. The concentration [BSA] of the BSA is accordingly determined by subtracting the effect of this absorption. Here $Ab_{280,BSA}$ represents the absorbance attributed to the BSA at 280 nm, the molar absorption coefficient of the SLIC1 at 280 nm is set equal $9.8\times10^3$, and the molar absorption coefficient of the BSA at 280 nm is $4.36\times10^4$.

$$Ab_{280,BSA}=9.6-(5.9\times10^{-4}\times9.8\times10^3)=3.818$$

$$[BSA]=3.818/4.36\times10^4=8.76\times10^{-5}\ (M)$$

The number of SLIC1 molecules bound to one BSA molecule accordingly given by:

$$[SLIC1]/[BSA]=5.9\times10^{-4}/8.76\times10^{-5}=6.7$$

(3) Reducing BSA-SLIC1 with DTT

The process added 100 mg of DTT (final concentration: 50 mm dissolved in 1 ml of PBS to the BSA-SLIC1 solution (110 mg, 13 ml) and stirred the mixed solution at room temperature for 15 minutes. The process quickly filtered the mixed solution through a gel, Sephadex G25M column. This gave approximately 24 ml of the PBS solution containing the BSA-SLIC1 (SH-free).

(4) Preparing Dye-Labeled Protein Conjugate

The (SH-free) BSA-SLIC1 solution and the SPDP-labeled IgG solution were mixed, stirred overnight at 4° C., and dialyzed against 20 liters of the PBS Az in order to remove unreacted BSA-SLIC1. This gave approximately 30 ml of the PBS solution containing the dye-labeled protein conjugate. The number of SLIC1 molecules bound to one molecule of the protein conjugate in the SLIC1-labeled protein conjugate was determined according to the following procedure.

The observed absorbance of the resultant solution at 430 nm was 30.2. The IgG does not have absorption at 430 nm, so that the observed absorbance at 430 nm is attributed to the SLIC1 bound to the BSA. The concentration [SLIC1] of the SLIC1 is thus determined by the following equation. Here the molar absorption coefficient of SLIC1 at 430 nm is set equal to $1 \times 10^5$.

$$[SLIC1] = 30.2/1 \times 10^5 = 3.02 \times 10^{-4} \text{ (M)}$$

The number of SLIC1 molecules bound to one molecule of the protein conjugate is calculated by the following equation:

$$[SLIC1]/[IgG] = 3.02 \times 10^{-4}/8.20 \times 10^{-7} = 368$$

where the concentration [IgG] of IgG in the PBS solution containing the SLIC1-labeled protein conjugate is set equal to $8.20 \times 10^{-7}$ M (on the assumption that there is no loss of IgG in each step after the SPDP labeling).

As described above, in the dye-labeled protein conjugate of the preset invention, the number of dye molecules bound to one protein molecule is approximately 10 times that in the conventional single body of the antibody. When the dye-labeled protein conjugate of the present invention is applied for an immunochromatography sensor, the immunochromatography sensor has a preferably high sensitivity.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A dye-labeled protein conjugate comprising a protein, an antibody bound to said protein via a disulfide bond to form a protein conjugate, and a cyanine dye represented by the following formula (1):

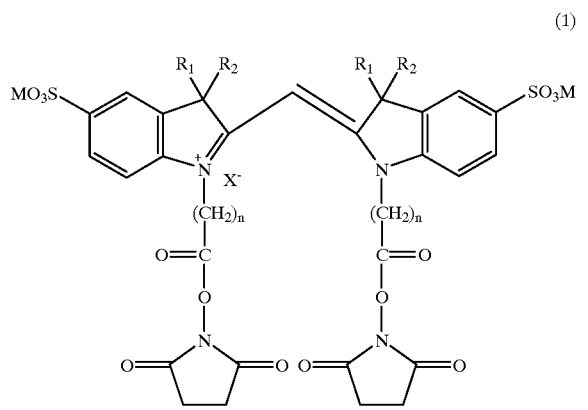

(1)

where $R_1$ and $R_2$ denote hydrogen or an alkyl group, X denotes a halogen, M denotes hydrogen or an alkali metal, and n represents an integer in a range of 1 to 4,
said protein conjugate being labeled with said cyanine dye, wherein said cyanine dye is bound to said protein conjugate via a covalent bond of an acyl carbon derived from a succinimidyl group present in said cyanine dye with a nitrogen derived from an amino group present in said protein conjugate.

2. A method for preparing a dye-labeled protein conjugate, said method comprising the steps of:
reducing a protein in a neutral or weak alkaline phosphate buffer solution;
adding an antibody to said buffer solution to prepare a protein conjugate; and
adding to said buffer solution a cyanine dye represented by the following formula (1) to label said protein conjugate with said cyanine dye:

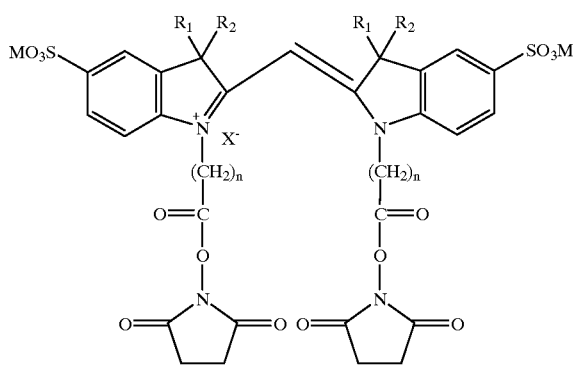

(1)

where $R_1$ and $R_2$ denote hydrogen or an alkyl group, X denotes a halogen, M denotes hydrogen or an alkali metal, and n represents an integer in a range of 1 to 4,
wherein said cyanine dye is bound to said protein conjugate via a covalent bond of an acyl carbon derived from a succinimidyl group present in said cyanine dye with a nitrogen derived from an amino group present in said protein conjugate.

3. A method for preparing a dye-labeled protein conjugate, said method comprising the steps of:
reducing a protein in a neutral or weak alkaline phosphate buffer solution;
adding a cyanine dye represented by the following formula (1) to said buffer solution to label the reduced protein with said cyanine dye;

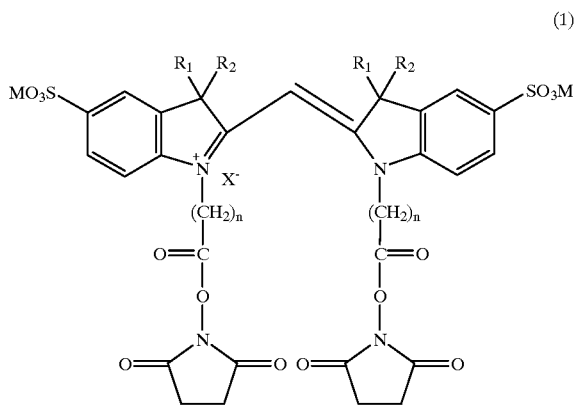

(1)

where $R_1$ and $R_2$ denote hydrogen or an alkyl group, X denotes a halogen, M denotes hydrogen or an alkali metal, and n represents an integer in a range of 1 to 4; and
adding an antibody to said buffer solution to bind said antibody to the reduced protein, wherein said cyanine dye is bound to said protein conjugate via a covalent bond of an acyl carbon derived from a succinimidyl group present in said cyanine dye with a nitrogen derived from an amino group present in said protein conjugate.

* * * * *